United States Patent
Schmidt

(10) Patent No.: US 8,348,833 B2
(45) Date of Patent: Jan. 8, 2013

(54) METHOD FOR CONTROLLING THE MOVEMENT OF AN ENDOSCOPIC CAPSULE

(75) Inventor: Sebastian Schmidt, Weisendorf (DE)

(73) Assignee: Siemens Aktiengesellschaft, Munich (DE)

( * ) Notice: Subject to any disclaimer, the term of this patent is extended or adjusted under 35 U.S.C. 154(b) by 156 days.

(21) Appl. No.: 12/937,752

(22) PCT Filed: Mar. 25, 2009

(86) PCT No.: PCT/EP2009/053536
§ 371 (c)(1),
(2), (4) Date: Oct. 14, 2010

(87) PCT Pub. No.: WO2009/127506
PCT Pub. Date: Oct. 22, 2009

(65) Prior Publication Data
US 2011/0054255 A1 Mar. 3, 2011

(30) Foreign Application Priority Data
Apr. 14, 2008 (DE) .......................... 10 2008 018 723

(51) Int. Cl.
*A61B 1/00* (2006.01)
(52) U.S. Cl. .......................... 600/118; 600/114; 600/117
(58) Field of Classification Search .................. 600/103, 600/114, 117, 118, 146, 424; 128/899
See application file for complete search history.

(56) References Cited

U.S. PATENT DOCUMENTS

| 4,824,205 | A  | * | 4/1989  | Yamashita et al. | 385/104 |
| 6,858,003 | B2 | * | 2/2005  | Evans et al.     | 600/103 |
| 7,173,507 | B2 |   | 2/2007  | Ries             |         |
| 7,798,958 | B2 | * | 9/2010  | Kawano et al.    | 600/118 |
| 8,050,738 | B2 | * | 11/2011 | Minai et al.     | 600/424 |
| 8,241,206 | B2 | * | 8/2012  | Kawano           | 600/117 |
| 2003/0055410 | A1 | * | 3/2003 | Evans et al.     | 606/1   |
| 2003/0060702 | A1 |   | 3/2003 | Kuth et al.      |         |
| 2005/0062562 | A1 |   | 3/2005 | Ries             |         |
| 2005/0093544 | A1 |   | 5/2005 | Ries             |         |
| 2007/0185398 | A1 | * | 8/2007 | Kimura et al.    | 600/424 |
| 2007/0265496 | A1 |   | 11/2007 | Kawano et al.   |         |
| 2008/0039688 | A1 | * | 2/2008 | Minal et al.     | 600/117 |
| 2008/0281188 | A1 | * | 11/2008 | Aoki et al.     | 600/424 |
| 2010/0168518 | A1 | * | 7/2010 | De Mathelin et al. | 600/118 |

* cited by examiner

*Primary Examiner* — John P Leubecker
(74) *Attorney, Agent, or Firm* — Schiff Hardin LLP

(57) ABSTRACT

In a method to control the movement of an endoscopy capsule in a hollow organ of a patient using a magnet system, a movement signal of the endoscopy capsule in the hollow organ is detected, that represents the time curve of the spatial position. The movement signal is evaluated to identify a periodic signal component thereof, and the frequency of this periodic signal component is identified. The magnet system is operated to exert a force on the endoscopy capsule in the hollow organ that is periodic with the frequency of the periodic signal component, and that is directed opposite to the movement signal.

9 Claims, 2 Drawing Sheets

FIG 2
a)
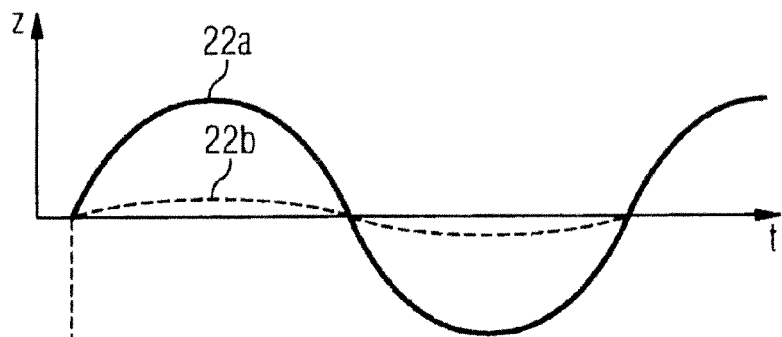
b)
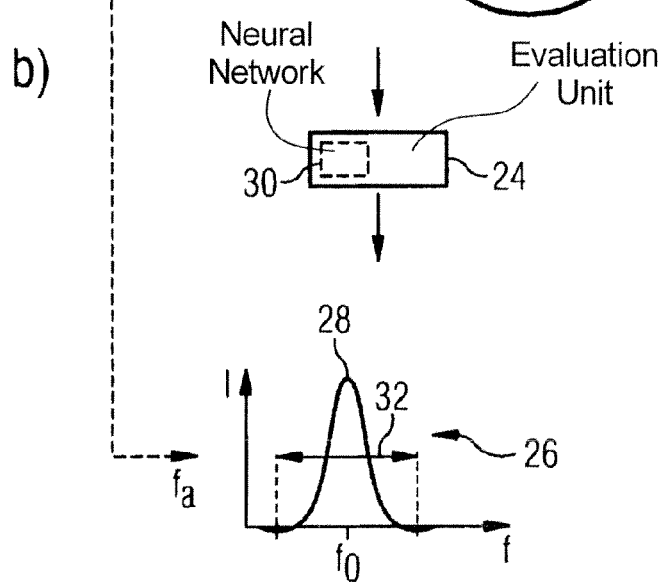
c)
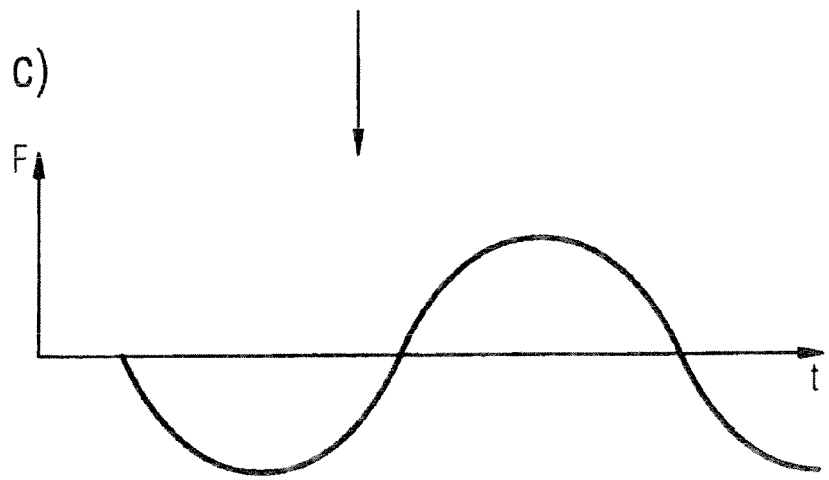

METHOD FOR CONTROLLING THE MOVEMENT OF AN ENDOSCOPIC CAPSULE

BACKGROUND OF THE INVENTION

1. Field of the Invention

The invention concerns a method to control the movement of an endoscopy capsule.

2. Description of the Prior Art

Non-invasive and minimally invasive medical procedures are continually gaining importance in medical technology. "Medical procedures" here is to be understood as an umbrella term for the most varied medical undertakings, for example visual examination or biopsies or therapies, for example targeted pharmaceutical administration or the attachment of clips or stents. Humans and animals are considered as patients on whom the medical procedure is conducted. The implementation of procedures inside the patient, particularly inside hollow organs (such as the entire gastrointestinal tract) is particularly desirable.

For this purpose, it is known to employ an endoscopy capsule which navigates (thus is moved) wirelessly inside the patient by means of controlled, external magnetic fields, as described in DE 101 42 253 C1. The endoscopy capsule is a capsule whose geometric dimensions are adapted to the hollow organ to be examined. The capsule persists inside the hollow organ (i.e. doesn't dissolve) and is equipped with one or more installed components, for example a video camera, a biopsy pincer or a medicine reservoir.

A suitable magnetic coil system to generate the magnetic fields is known from DE 103 40 925 B3, for example. The magnetic fields are generated by a magnet system or coil system surrounding the patient, the magnet system or coil system being composed of multiple (for example fourteen) individual electrical coils. The magnetic fields induced by the magnet system generate a translational force, or a torque at a magnetic element attached in the capsule, and thus moves the capsule in the patient. The force exertion or movement in the patient thus ensues in a directed manner, without contact, and monitored or controlled from the outside.

In such an examination method at the patient—for example with an aforementioned system, known as controlled capsule endoscopy—that is conducted in the stomach, for example, the capsule typically swims on a fluid surface. This fluid surface moves due to external influences, for example heart beat, breathing or peristalsis of the patient. Surface waves form on the fluid surface, the surface waves being reflected at the wall of the hollow organ (for example the stomach) so that fast standing surface waves arise given a suitable wavelength. The capsule is picked up by these surface waves and thus moves up and down at least perpendicular to the averaged surface. In other words, the capsule bobs on the fluid surface. Typical frequencies for such capsule movements are in the range of a few hertz. Such a movement or rocking of the capsule negatively affects the finding quality of the examination method. For example, video exposures generated by the capsule are unsteady.

In general the movement of the capsule is monitored by, for example, the aforementioned magnet system. For this purpose, the spatial position or the time/space curve or the movement of the capsule is detected by a position detection system. Furthermore, a desired position for the capsule in the patient is externally predetermined, for example by a treating physician. Given deviation of the actual spatial position from the predetermined desired position, corresponding fields are automatically generated in the magnet system by a feedback mechanism in order to generate suitable fields in order to move the capsule to the desired position or keep it constant there.

The cited movement control is designed for arbitrary, normally aperiodical or relatively slow movements of the capsule for example just the targeted movement of the capsule through the patient or holding the capsule at a desired position in the patient. A disadvantage of this known system and method for movement control of the capsule is the inertia of the position detection system and magnet system. For the aforementioned swaying or bobbing of the capsule on a fluid surface, for example, in the most disadvantageous case the delay of the aforementioned feedback regulation corresponds to precisely half of the period of the movement of the capsule that is generated by the surface waves. The generated field (which is thus time-delayed due to the inertia) and therefore the force that acts on the capsule thus does not counteract the movement of the capsule but rather reinforces this movement, even in the sense of a resonance (constructive interference). Keeping the capsule at rest or attenuating the oscillation of the capsule is impossible in such a case.

SUMMARY OF THE INVENTION

An object of the present invention to specify an improved method to control the movement of an endoscopy capsule.

The object is achieved by a method to control the movement of an endoscopy capsule, wherein the capsule is located in a hollow organ of a patient, and wherein the movement of the capsule ensues using a magnet system. The method according to the invention includes the following steps. A movement signal is detected which reflects the time curve of the spatial position of the capsule. The detected movement signal is examined for a periodic signal portion. If the periodic signal portion is found, its frequency is determined. The magnet system subsequently exerts a force on the endoscopy capsule that is periodic with the frequency that was just determined and directed opposite the movement signal.

In other words, periodic oscillations or movements of the endoscopy capsule are identified according to the invention by detecting the periodic signal component. In order to compensate or attenuate this, a suitable periodic counter-force is generated at the capsule with the use of the magnet system, which counter-force actively damps the oscillations of the capsule. A force directed counter to the respective movement of the capsule during the oscillation is thus generated.

An active oscillation damping for periodic (i.e. nearly monofrequency) oscillations of a magnetically navigated endoscopy capsule ensues via application of the method according to the invention. Naturally, multiple monofrequency portions can also be overlaid to form a complex periodic oscillation. A movement of the capsule that is reduced overall results from this, thus a smoother flotation and therefore (for example in the case of imaging by the capsule) a more steady (and therefore improved) image or moving image acquired by the capsule.

The advantage relative to the method according to the prior art is that the periodicity of the capsule movement is detected and generation of a filed with a corresponding period ensues in the magnet system. In this periodicity the inertia of the entire navigation system (or the corresponding delay time between position detection and magnetic field generation) can be taken into account through a suitable phase shift, at least for the period portion. In a certain manner the advantage is utilized that the future capsule movement or movement component can be predicted (at least with regard to this movement portion) given a periodic oscillation of the capsule, and corresponding predictive fields or counter-forces can be generated by the magnetic field system to damp oscillation.

For a given examination case with a given patient, only specific maximum frequencies for periodic movements of the capsule can be expected due to prior knowledge or, respectively, experimental values from preceding applications of endoscopy capsules. In a preferred embodiment of the method, the movement signal can then ensue through a periodic detection or sampling of the spatial position of the capsule, wherein this sampling is implemented with at least twice the frequency of what is to be expected as the maximum frequency of the periodic movement of the capsule. The digital sampling theorem is thus satisfied and no errors can occur in the determination of the spatial curve of the capsule position.

In a further advantageous embodiment, the examination of the movement signal for the periodic signal portion ensues using a Fourier transformation and/or the frequency spectrum of the movement signal. Characteristic periodic signal components can be differentiated particularly simply from aperiodic signal portions and thus be detected.

In a further advantageous embodiment, the periodic signal component can be identified particularly simply by seeking or determining a peak that is elevated locally above the Fourier and/or frequency spectrum. Such a peak is, for example, an elevation in a graphically plotted spectrum that, according to commonly known criteria, characteristically rises locally above the remaining spectrum.

As an alternative or in addition to the aforementioned methods, in a further advantageous embodiment the movement signal can be examined for the periodic signal component with the aid of a neural network. For this purpose, for example, a neural network is trained specifically for the appertaining task, thus the identification of period signal portions in the movement signal of the endoscopy capsule. Given a known period signal component, the neural network can alternatively or additionally be used to determine the appertaining suitable damping signal, thus the time curve of the of the force to be generated by the magnet system and directed counter to the periodic movement signal.

In another advantageous embodiment the movement signal is examined for a periodic signal component only in a predeterminable frequency range. In other words, the realization that periodic oscillations of the endoscopy capsule are not expected in specific frequency ranges is utilized. Such frequency ranges then also do not have to be examined for the occurrence of periodic signal portions. The corresponding search in predeterminable frequency ranges is thereby accelerated.

In a further preferred embodiment, that frequency range that corresponds to an eigenfrequency of the magnet system can be selected as such a frequency range. Such eigenfrequencies are, for example, those that correspond to the inertia or, delay time of the magnet system between spatial detection and magnetic field generation, or other typical eigenfrequencies of the magnet system would in disadvantageous cases could lead to resonance fluctuations at the endoscopy capsule. In other words, known system-induced oscillation frequencies or other typical oscillation frequencies that occur frequently (based on experimental values, for example) are thus specifically observed in this development of the method in order to counteract these. In the case of a Fourier spectrum, for example, this means that only specific regions of this are examined or observed in order to detect periodic signal components.

BRIEF DESCRIPTION OF THE DRAWINGS

FIG. 2, in part a), shows the time curve of the spatial position of the endoscopy capsule in FIG. 1, and in part b) shows the frequency spectrum of the signal from a), and in part c) shows the time curve of the counter-force generated by the magnet system in FIG. 1.

DESCRIPTION OF THE PREFERRED EMBODIMENTS

Figure 1:
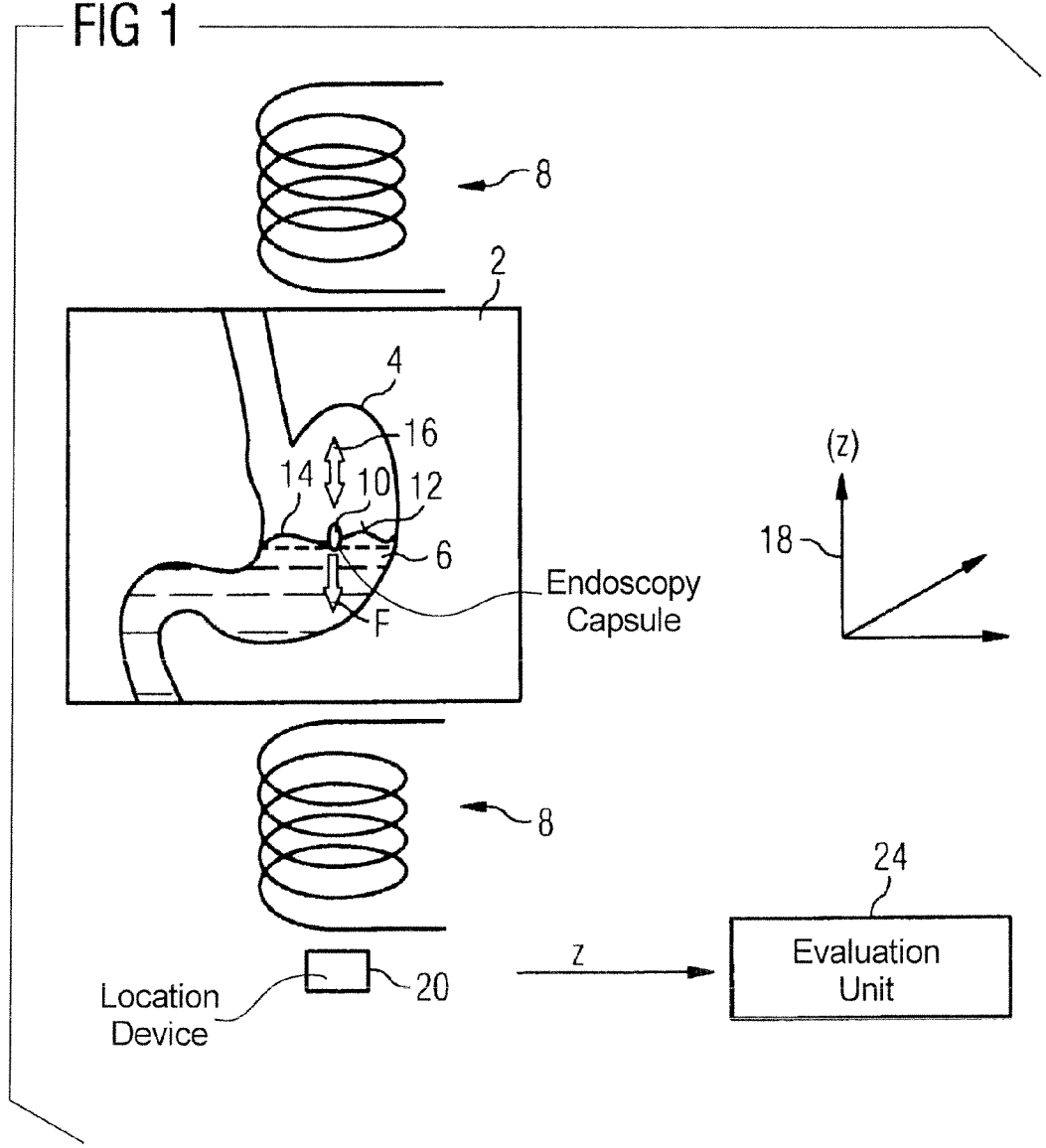
FIG. 1 schematically illustrates a sectional view of a patient during a capsule endoscopy procedure.

FIG. 1 shows a section of a patient 2 (namely the stomach 4) which is approximately half-filled with fluid 6. The patient 2 is located in a situation during a capsule endoscopy wherein he is borne in a magnet coil system 8 (which is symbolically represented by two magnet coils). Moreover, for capsule endoscopy an endoscopy capsule 10 is administered to the patient 2, which endoscopy capsule 10 is now located in the stomach 4. Due to various influencing factors—for example heart beat, breathing and peristalsis of the patient 2—the fluid 6 of the stomach 4 is in motion and forms waves 14 on its surface 12. Due to the waves 13 the endoscopy capsule 10 (which floats on the surface 12) moves up and down in the stomach 4 in the direction of the double arrow 16. The movement therefore ensues along a z-axis of a coordinate system 18 of the magnet coil system 8.

The magnet coil system 8 has a location device 20 to determine the spatial position of the endoscopy capsule 10 in the coordinate system 18. Moreover, the current spatial position z is determined relative to the z-axis. The spatial position is transmitted to a control and evaluation unit 24 and recorded there over time as a movement signal 22a.

Part a) of FIG. 2 shows the curve of the spatial position z of the endoscopy capsule 10 over time t in the movement signal 22a. The movement signal 22a is processed by the control and evaluation unit 24 which determines its frequency spectrum 26 (which is shown in part b) of FIG. 2). The intensity I of the respective frequency portions of the total signal is plotted over the frequency f. Since the movement signal 22a proceeds nearly sinusoidally with constant frequency $f_0$ and the endoscopy capsule 10 otherwise executes no additional superimposed movements in the stomach 4, the frequency spectrum 26 is represented as a peak 28 around the peak $f_0$. In the frequency spectrum 26 the peak 28 therefore represents a periodic signal portion in the movement signal 22a.

Using the frequency spectrum 26, the control and evaluation unit 24 detects that the endoscopy capsule 10 moves periodically with the frequency $f_0$ and generates corresponding magnetic fields in the magnet coil system 8 in order to generate a force F at the endoscopy capsule 10, the force being directed counter to the current movement of the endoscopy capsule 10 (known from the movement signal 22a) at every point in time t, as shown in part c) of FIG. 2.

Part c) of FIG. 2 shows the time curve of the generated force F over time t. The movement of the endoscopy capsule 10 in the direction of the double arrow 16 is strongly attenuated by the force F, which is why a movement signal 22b (which is shown with a dashed line in Part a) of FIG. 2) henceforth results for the endoscopy capsule 10.

The movement portion of the endoscopy capsule 10 that is periodic with the frequency $f_0$ is thus nearly eliminated by the described method, meaning that this endoscopy capsule 10 is held nearly stationary in the z-direction of the coordinate system 18 in the stomach 4. This leads to a significantly improved functionality of the endoscopy capsule 10 if this delivers a video image of the inside of the stomach 4, for example, which video image fluctuates severely according to movement signal 22a and is now nearly at rest according to movement signal 22b.

In an alternative embodiment, the control and evaluation unit 24 can contain a neural network 30 to handle the aforementioned tasks of the signal processing and force generation.

In an alternative embodiment, the frequency spectrum 26 is determined by sampling the movement signal 22a with a sampling frequency $f_a$. For the examination situation shown in FIG. 1 it is hereby known that the maximum occurring frequency of an oscillation of the endoscopy capsule 10 is the frequency $f_0$. The sampling frequency $f_a$ is therefore selected according to the sampling theorem at $f_a \geq 2f_0$.

In a further alternative embodiment, only the frequency range 32 is examined by the control and evaluation unit 24 for periodic signal portions since no periodic signal portions are to be expected in the remaining frequency range of the frequency spectrum 26 based on experimental values with the magnet coil system 8. Such capsule oscillations namely do not occur.

Although modifications and changes may be suggested by those skilled in the art, it is the intention of the inventor to embody within the patent warranted heron all changes and modifications as reasonably and properly come within the scope of his contribution to the art.

I claim:

1. A method to control movement of an endoscopy capsule in a hollow organ of a patient using a magnet system, comprising the steps of:
    detecting a movement signal representing a time curve of the spatial position of the endoscopy capsule in the hollow organ;
    evaluating the movement signal to identify a periodic signal component thereof;
    identifying a frequency of said periodic signal component; and
    with said magnet system, generating and exerting a force on said endoscopy capsule in the hollow organ that is periodic with said frequency of said periodic signal component and has a magnitude opposite to a magnitude of said movement signal.

2. A method as claimed in claim 1 wherein said endoscopy capsule in said hollow organ has an expected periodic movement associated therewith exhibiting an expected periodic movement frequency, and comprising detecting said movement signal of said endoscopy capsule with a sampling frequency that is at least twice the expected periodic movement frequency.

3. A method as claimed in claim 1 comprising evaluating said movement signal to identify said periodic signal component thereof by Fourier transforming said movement signal.

4. A method as claimed in claim 3 wherein Fourier transforming said movement signal produces a local peak that is elevated above the Fourier spectrum, and identifying said local peak as representing said periodic signal component.

5. A method as claimed in claim 1 comprising evaluating said movement signal to identify said periodic signal component by spectral analysis of a frequency spectrum of said movement signal.

6. A method as claimed in claim 5 comprising in said spectral analysis, identifying a local peak that is elevated above the frequency spectrum, and identifying said local peak as said periodic signal component.

7. A method as claimed in claim 1 comprising evaluating said movement signal to identify said periodic signal component thereof in a neural network.

8. A method as claimed in claim 1 comprising evaluating said movement signal only in a predetermined frequency range to identify said periodic signal component thereof.

9. A method as claimed in claim 8 wherein said magnet system has an eigenfrequency, and comprising using said eigenfrequency of said magnet system as said frequency range.

* * * * *